US010118110B2

(12) United States Patent
Shinohata et al.

(10) Patent No.: US 10,118,110 B2
(45) Date of Patent: Nov. 6, 2018

(54) REACTION METHOD ACCOMPANIED BY PRODUCTION OF GAS COMPONENT

(71) Applicant: Asahi Kasei Chemicals Corporation, Tokyo (JP)

(72) Inventors: Masaaki Shinohata, Tokyo (JP); Takeharu Sasaki, Tokyo (JP); Nobuhisa Miyake, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 0 days.

(21) Appl. No.: 14/908,698

(22) PCT Filed: Jul. 30, 2014

(86) PCT No.: PCT/JP2014/070069
§ 371 (c)(1),
(2) Date: Jan. 29, 2016

(87) PCT Pub. No.: WO2015/016263
PCT Pub. Date: Feb. 5, 2015

(65) Prior Publication Data
US 2016/0166950 A1 Jun. 16, 2016

(30) Foreign Application Priority Data

Aug. 2, 2013 (JP) .................................. 2013-161172

(51) Int. Cl.
*C07C 67/08* (2006.01)
*B01D 19/00* (2006.01)
(Continued)

(52) U.S. Cl.
CPC .......... *B01D 19/0042* (2013.01); *B01J 14/00* (2013.01); *B01J 19/00* (2013.01); *C07C 67/08* (2013.01);
(Continued)

(58) Field of Classification Search
None
See application file for complete search history.

(56) References Cited

U.S. PATENT DOCUMENTS

2005/0223847 A1 10/2005 Shiraishi et al.
2006/0090651 A1* 5/2006 Liu .................... B01D 46/0021
96/121
(Continued)

FOREIGN PATENT DOCUMENTS

JP S49-034480 A 3/1974
JP H07-157463 A 6/1995
(Continued)

OTHER PUBLICATIONS

English Translation of Yamawaki et al. (JP 08277255).*
(Continued)

*Primary Examiner* — Sudhakar Katakam
*Assistant Examiner* — Jennifer C Sawyer
(74) *Attorney, Agent, or Firm* — Morgan, Lewis & Bockius LLP

(57) ABSTRACT

The present invention relates to a reaction method comprising a step of supplying a liquid containing at least one raw material compound and a low-boiling compound having a standard boiling point lower than a standard boiling point of the raw material compound to a flow channel, a step of heating the liquid to produce a liquid reaction product and a gas component by a reaction of the raw material compound, and a step of separating a liquid phase containing the reaction product from a gas phase containing the gas component and the low-boiling compound.

15 Claims, 1 Drawing Sheet

(51) Int. Cl.
- *B01J 14/00* (2006.01)
- *B01J 19/00* (2006.01)
- *C07C 263/06* (2006.01)
- *C07C 265/14* (2006.01)
- *C07C 269/00* (2006.01)
- *C07C 269/04* (2006.01)
- *C07C 271/44* (2006.01)
- *C07C 271/52* (2006.01)
- *C07C 69/14* (2006.01)
- *C07C 271/02* (2006.01)

(52) U.S. Cl.
CPC ............ *C07C 69/14* (2013.01); *C07C 263/06* (2013.01); *C07C 265/14* (2013.01); *C07C 269/00* (2013.01); *C07C 269/04* (2013.01); *C07C 271/02* (2013.01); *C07C 271/44* (2013.01); *C07C 271/52* (2013.01)

(56) References Cited

U.S. PATENT DOCUMENTS

| | | |
|---|---|---|
| 2008/0227999 A1 | 9/2008 | Molzahn |
| 2009/0087683 A1 | 4/2009 | Shiraishi et al. |

FOREIGN PATENT DOCUMENTS

| | | |
|---|---|---|
| JP | H08-277255 A | 10/1996 |
| JP | H10-000301 A | 1/1998 |
| JP | 2002-142747 A | 5/2002 |
| JP | 2005-224764 A | 8/2005 |
| JP | 2006-272131 A | 10/2006 |
| JP | 2006-272132 A | 10/2006 |
| JP | 2008-168173 A | 7/2008 |
| JP | 2009-502792 A | 1/2009 |
| WO | 2006/104241 A1 | 10/2006 |

OTHER PUBLICATIONS

European Search Report issued in counterpart European Patent Application No. 14832812.3 dated Jun. 27, 2016.
Ichikawa et al., "Micro-reactors for liquid-liquid reactions," Database CA [online], Chemical Abstracts Service, XP002758795 (2005).
International Preliminary Report on Patentability and Written Opinion issued in counterpart International Patent Application No. PCT/JP2014/070069 dated Feb. 11, 2016.
International Search Report issued in counterpart International Patent Application No. PCT/JP2014/070069 dated Oct. 21, 2014.
CDTECH MTBE Process Technology, 57: 77-79 (1993) (see English abstract).

* cited by examiner

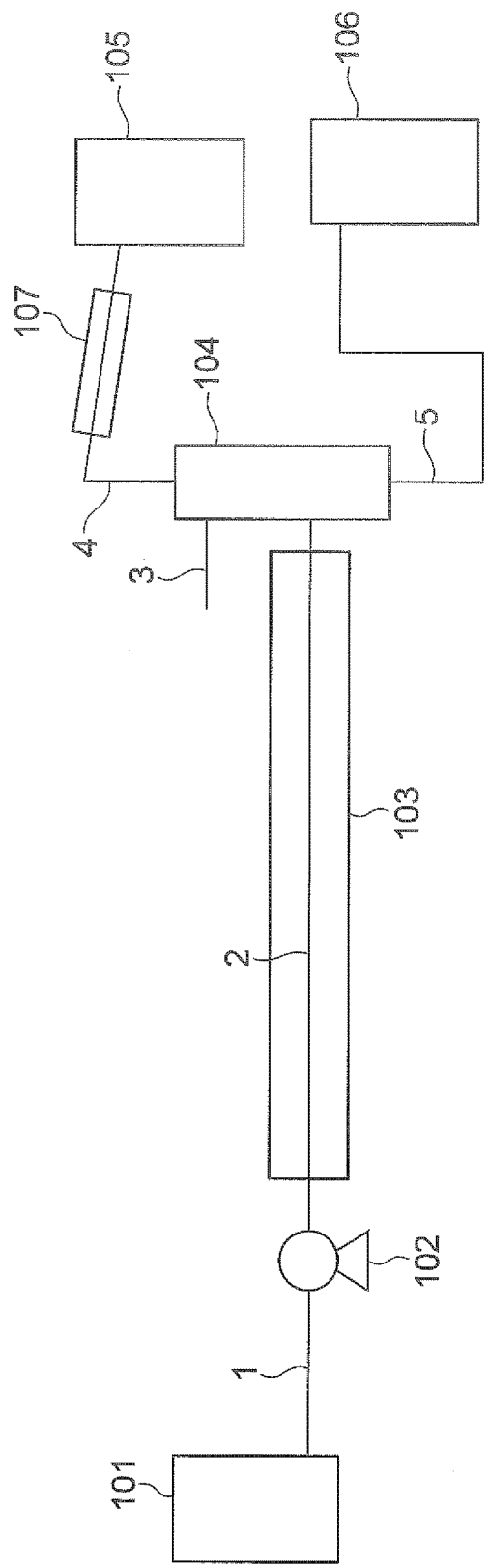

REACTION METHOD ACCOMPANIED BY PRODUCTION OF GAS COMPONENT

TECHNICAL FIELD

The present invention relates to a method for efficiently performing an equilibrium reaction accompanied by production of a gas component.

BACKGROUND ART

Many reactions among conventionally performed reactions are equilibrium reactions in each of which a forward reaction and a backward reaction exist at a certain constant rate. When the equilibrium of an equilibrium reaction is unfavorable for a product system side, at least one of products is generally separated from a reaction system to make the above-described equilibrium favorable for the product system favorable to increase reaction efficiency (equilibrium conversion rate). Various methods are known as a method of separating a product from a reaction system, and distillation separation is one of the most commonly performed methods. A method in which an equilibrium reaction is shifted to a product side to progress a reaction while removing a product from a reaction system by distillation is called reactive distillation, and for example, the explanation of reactive distillation is described in Non Patent Literature 1 by providing specific examples.

In general, reactive distillation is performed by using a distillation column such as a continuous multistage distillation column (reactive distillation equipment). When reactive distillation is performed in the distillation column, with the progress of a reaction, a higher-boiling component contained in a reaction liquid is distributed more in a lower stage side of the distillation column, whereas a lower-boiling component contained in the reaction liquid is distributed more in an upper stage side of the distillation column. Therefore, in the distillation column, the temperature in the column (liquid temperature) decreases from the bottom to the top of the column. The reaction rate of an equilibrium reaction decreases as the temperature becomes lower. For this reason, when reactive distillation is performed in the above-described distillation column, the reaction rate decreases from the bottom to the top of the column. More specifically, when reactive distillation is performed in the distillation column, the reaction efficiency of the equilibrium reaction decreases from the bottom to the top of the column.

In order to further improve the reaction efficiency, that is, to increase the reaction rate, a further increase in the temperature in the column has been studied. For example, Patent Literature 1 discloses a method of advantageously progressing a reaction by supplying a solvent to a reactive distillation column to raise the temperature in the reactive distillation column, as a method of efficiently performing an equilibrium reaction represented by Raw Material (P)+Raw Material (Q)⇔Product (R)+Product (S), especially, an ester exchange reaction.

Moreover, use of a flow channel forming body called a micro channel reactor as reaction equipment for increasing the yield and the purity of a reaction product and safely performing a risky reaction is known (refer to Patent Literature 2). Since the micro channel reactor can efficiently transfer heat compared to an ordinary reaction container, a risky reaction such as nitration is perceived to be safely performed even at a high temperature. In addition, heating and cooling of a reaction system can be performed quickly, and the reaction can be easily controlled. Although the amount of a compound that can be handled with a micro channel reactor used in a laboratory is low, scale-up for industrial processes is possible by increasing the number of micro channels. Therefore, if the reactive distillation described above can be performed using a micro channel reactor, industrial value is high.

However, there is a problem in that a reaction in which some components become gases, such as reactive distillation, cannot be performed by a method using a micro channel reactor. This is because, in the continuous multistage distillation column (reactive distillation equipment) described above, a gas component is constantly extracted from a liquid phase, and thus, the concentration in the liquid phase becomes lower than the equilibrium value, and the equilibrium of an intended reaction can be shifted to a product side, but in the micro channel reactor, bubbles of generated gas are retained in a flow channel, and thus, the concentration of a gas component in a liquid phase achieves equilibrium due to the gas-liquid equilibrium of the gas component in the flow channel, and the equilibrium of a reaction to be performed is dominated by the concentration in the liquid phase.

With respect to this problem, for example, Patent Literature 3 discloses a method in which a reaction is performed while supplying gas to a flow channel to form a gas layer above a liquid phase in the flow channel, and making a by-product gas be trapped in the gas layer to be discharged out of the flow channel together with the gas layer. This method is intended to stabilize the liquid flow in the flow channel and shift the equilibrium of the reaction to a product side by making the by-product gas generated by the reaction be immediately trapped in the gas layer to be discharged out of the flow channel.

CITATION LIST

Patent Literature

Patent Literature 1: JP 10-301 A
Patent Literature 2: JP 2008-168173 A
Patent Literature 3: JP 2005-224764 A Non Patent Literature Non Patent Literature 1: "Chemical Engineering", Vol. 57, No. 1, pp. 77-79 (1993)

SUMMARY OF INVENTION

Technical Problem

However, the control of the gas layer and the liquid layer in the flow channel is difficult in the method disclosed in Patent Literature 3. Moreover, an opening for introducing gas into the flow channel and discharging it out of the flow channel and an opening for introducing a liquid into the flow channel and discharging it out of the flow channel need to be provided, and designing and processing of equipment itself are difficult. The number of flow channels is increased in the case of industrial practice, but the control of a gas layer and a liquid layer and processing of equipment are required for each flow channel, and thus, the method is unsuitable for industrial practice.

It is an object of the present invention to provide a reaction method capable of efficiently collecting a reaction product with simple equipment.

Solution to Problem

The present inventors made extensive research, and as a result, found that the above-described problem can be solved by a method in which, to a flow channel in which a reaction is performed, a liquid containing a raw material compound and a low-boiling compound which forms a gas phase by heating in the flow channel are supplied, the gas phase containing the low-boiling compound is formed in the flow channel, a gas component produced by the reaction is extracted into the gas phase, and the gas component produced by the reaction is discharged out of the flow channel together with the low-boiling compound, to complete the present invention.

More specifically, the present invention provides the followings.

[1] A reaction method accompanied by production of a gas component, comprising a step of supplying a liquid containing at least one raw material compound and a low-boiling compound having a standard boiling point lower than a standard boiling point of the raw material compound to a flow channel, a step of heating the liquid to produce a liquid reaction product and a gas component by a reaction of the raw material compound, and a step of separating a liquid phase containing the reaction product from a gas phase containing the gas component and the low-boiling compound.

[2] The method according to [1], wherein a stoichiometric proportion of the raw material compound to the reaction product in the liquid is raw material compound:reaction product=100:0 to 80:20.

[3] The method according to [1] or [2], wherein the flow channel has a specific surface area of 10 m²/m³ or more and less than 1000 m²/m³.

[4] The method according to any one of [1] to [3], wherein the low-boiling compound is collected as a component contained in the gas phase and/or the liquid phase.

[5] The method according to any one of [1] to [4], wherein the gas phase containing the gas component and the low-boiling compound is produced in the flow channel.

[6] The method according to any one of [1] to [5], wherein the standard boiling point of the low-boiling compound is lower than the standard boiling point of the raw material compound by 10° C. or more.

[7] The method according to any one of [1] to [6], wherein the gas component contains at least one selected from the group consisting of water, ammonia, an amine compound, a hydroxy compound and a thiol compound.

[8] The method according to [7], wherein the gas component contains water, and the reaction includes at least one reaction selected from the group consisting of functional group reactions represented by formulas (1) and (2):

[Chemical Formula 1]

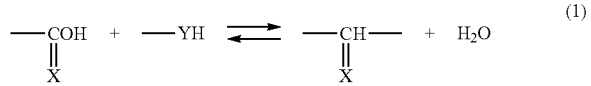

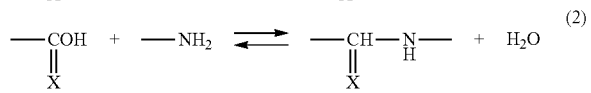

wherein X and Y each independently represents an oxygen atom or a sulfur atom.

[9] The method according to [7], wherein the gas component contains ammonia, and the reaction includes at least one reaction selected from the group consisting of functional group reactions represented by formulas (3) to (8):

[Chemical Formula 2]

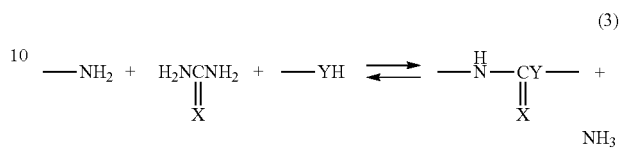

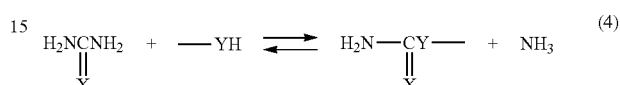

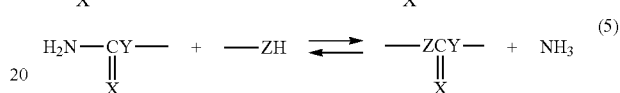

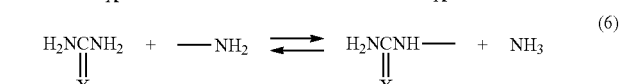

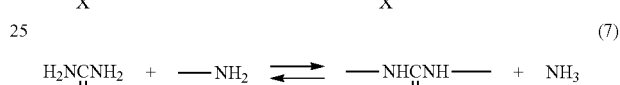

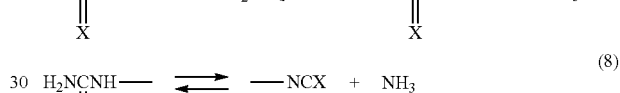

wherein X, Y and Z each independently represents an oxygen atom or a sulfur atom.

[10] The method according to [7], wherein the gas component contains an amine compound, and the reaction includes at least one reaction selected from the group consisting of functional group reactions represented by formulas (9) to (11):

[Chemical Formula 3]

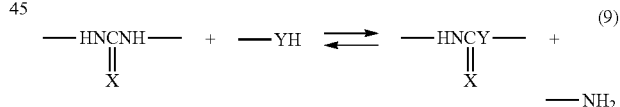

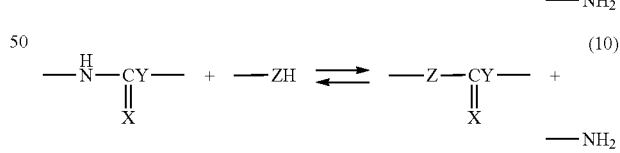

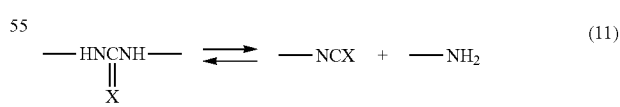

wherein X, Y and Z each independently represents an oxygen atom or a sulfur atom.

[11] The method according to [7], wherein the gas component contains a hydroxy compound or a thiol compound, and the reaction includes at least one functional group reaction selected from the group consisting of functional group reactions represented by formulas (12) and (13):

[Chemical Formula 4]

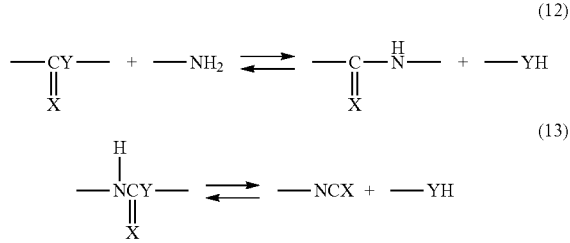

wherein X and Y each independently represents an oxygen atom or a sulfur atom.

[12] The method according to [7], wherein the gas component contains a hydroxy compound or a thiol compound, the reaction is an ester exchange reaction that is a reaction of a hydroxy compound or a thiol compound with an ester compound, and the ester compound is at least one ester selected from the group consisting of a carboxylate ester, a thiocarboxylate ester, a carbonate ester, a carbamate ester and a thiocarbamate ester.

[13] The method according to any one of [1] to [12], wherein the flow channel is heated to 80° C. or more, and the low-boiling compound is a compound having a standard boiling point of 50° C. or more.

[14] The method according to any one of [1] to [13], wherein an equivalent diameter of the flow channel is 50 mm or less.

[15] Equipment for performing the method according to any one of [1] to [14], wherein separation of the liquid phase containing the reaction product from the gas phase containing the gas component and the low-boiling compound is performed in a gas-liquid separator, and the flow channel at a connection between the gas-liquid separator and the flow channel is inclined at 5° or more to a horizontal surface.

[16] A reaction product obtained by the method according to any one of [1] to [14].

Advantageous Effects of Invention

According to the present invention, a reaction method capable of efficiently collecting a reaction product with simple equipment can be provided.

BRIEF DESCRIPTION OF THE DRAWINGS

FIG. 1 is a diagram schematically showing one embodiment of a reaction step.

DESCRIPTION OF EMBODIMENTS

Hereinafter, embodiments for carrying out the present invention (hereinafter, referred to as "present embodiments") will be described in detail. It is to be noted that the present invention is not limited to the following embodiments, and can be embodied in various ways within the scope of the present invention.

The present invention relates to a reaction method including a step of supplying a liquid containing at least one raw material compound and a low-boiling compound having a standard boiling point lower than the standard boiling point of the raw material compound to a flow channel (hereinafter, referred to as "supply step"), a step of heating the above-described liquid to produce a liquid reaction product and a gas component by a reaction of the raw material compound (hereinafter, referred to as "reaction step"), and a step of separating a liquid phase containing the reaction product from a gas phase containing the gas component and the low-boiling compound (hereinafter, referred to as "separation step").

FIG. 1 is a diagram schematically showing one embodiment of the reaction step according to the present embodiments. The reaction method of the present embodiments will be described using FIG. 1.

[Supply Step]

Firstly, a liquid containing at least one raw material compound and a low-boiling compound is supplied to a flow channel 1 from a tank 101. Next, the liquid which has been supplied to the flow channel 1 is supplied to a flow channel 2 by a pump 102.

[Reaction Step]

The flow channel 2 is heated by a heater 103. The liquid which has been supplied to the flow channel 2 is heated, and a reaction liquid containing a liquid reaction product and a gas component is produced by a reaction of the raw material compound.

<Raw Material Compound>

The raw material compound is composed of at least one compound, and is supplied to the flow channels 1 and 2 in liquid form. The raw material compound being in liquid form means that the boiling point is higher than the temperatures of the flow channels 1 and 2. The raw material compound exists in a liquid phase in the flow channel 1. It is to be noted that, in the liquid to be supplied to the flow channel 2, the stoichiometric proportion of the raw material compound to the reaction product is preferably raw material compound:reaction product=100:0 to 80:20.

<Low-Boiling Compound>

The low-boiling compound according to the present embodiments is a compound which has a standard boiling point lower than the standard boiling points of all raw material compounds and does not have reactivity with the raw material compounds. The low-boiling compound is turned into gas by heating in the flow channel 2 in which the reaction step is performed to form a gas phase. The standard boiling point of the low-boiling compound is preferably lower than the standard boiling point of the raw material compound by 10° C. or more. The low-boiling compound being gas indicates the case where the boiling point of the low-boiling compound is lower than the reaction temperature. Whether the low-boiling compound is a compound which forms a gas phase by heating in the flow channel 2 in which the reaction step is performed can be easily determined by those skilled in the art, for example, by reference to the vapor pressure of the compound, the standard boiling point of the compound and the like ire reaction conditions.

The low-boiling compound forms a gas phase in the flow channel 2, but is preferably a liquid when being supplied to the flow channel 2 in which the reaction step is performed together with a mixture containing the raw material compound. More specifically, the low-boiling compound is supplied to the flow channel 2 as a liquid, and forms a gas phase by heating in the flow channel 2. Effects by the use of the low-boiling compound are presumed as follows. Since the gas phase is formed in the flow channel 2, a gas-liquid equilibrium state is formed with the liquid phase (ideally, one theoretical distillation plate), the gas component produced by the reaction can be rapidly transferred to the gas phase from the liquid phase, and therefore, an effect of capable of shifting the equilibrium of the reaction to the product side is exerted.

Moreover, it is preferable that a compound which is compatible with the mixture containing the raw material compound to become a single solution be selected as the low-boiling compound, and after preparing a mixture containing the low-boiling compound and the raw material compound, the mixture be supplied to the flow channel 2. According to this method, the state of a gas-liquid multiphase flow in the flow channel 2 becomes stable, and effects of becoming easier to control the reaction, improving the reaction efficiency and the like are exerted.

The reaction step is preferably performed at 80° C. or more. More specifically, the flow channel 2 in which the reaction step is performed is heated to 80° C. or more. From the viewpoint of such a preferred reaction temperature and handling, the standard boiling point of the low-boiling compound is preferably 50° C. or more.

Examples of the low-boiling compound may include at least one compound selected from the group consisting of (A) hydrocarbon compounds having a straight-chain, branched-chain or cyclic structure, (B) compounds in which hydrocarbon compounds of the same kind or different kinds having a straight-chain, branched-chain, or cyclic structure are bonded via an ether bond or a thioether bond (i.e., compounds in which two hydrocarbon compounds are bonded via an ether bond or a thioether bond; the above-described hydrocarbon compounds have a straight-chain, branched-chain or cyclic structure, and the two hydrocarbon compounds may be the same kind or different kinds), (C) aromatic hydrocarbon compounds which may have a substituent comprising a hydrocarbon group, (D) compounds in which aromatic hydrocarbon compounds of the same kind or different kinds are bonded via an ether bond or a thioether bond, (E) compounds in which a hydrocarbon compound having a straight-chain, branched-chain or cyclic structure and an aromatic hydrocarbon compound are bonded via an ether bond or a thioether bond, (F) halides in which at least one hydrogen atom constituting a hydrocarbon compound having a straight-chain, branched-chain or cyclic structure, or at least one hydrogen atom constituting an aromatic hydrocarbon compound which may have a substituent comprising a hydrocarbon group is replaced by a halogen atom, and (G) hydroxy compounds (alcohols, aromatic hydroxy compounds).

Preferred specific examples of the low-boiling compound may include hydrocarbon compounds such as pentane, hexane, heptane, octane, nonane, decane, dodecane, tetradecane, pentadecane, hexadecane, octadecane and nonadecane; ethers such as dimethyl ether, diethyl ether, tetrahydrofuran and tetrahydropyran; thioethers in which hydrocarbon compounds are bonded via a thioether bond, such as dimethyl sulfide, diethyl sulfide, dibutyl sulfide and dihexyl sulfide; aromatic hydrocarbon compounds such as benzene, toluene, ethylbenzene, butylbenzene, pentylbenzene, hexylbenzene, biphenyl, diphenylethane, dimethylbiphenyl and benzyltoluene; aromatic ethers in which aromatic hydrocarbon compounds are bonded via an ether bond, such as diphenyl ether, di(methylbenzyl)ether, di(ethylbenzyl)ether, di(butylbenzyl)ether, di(pentylbenzyl)ether, di(hexylbenzyl)ether, di(octylbenzyl)ether and dibenzyl ether; aromatic thioethers in which aromatic hydrocarbon compounds are bonded via a thioether bond, such as diphenyl sulfide, di(methylbenzyl)sulfide, di(ethylbenzyl)sulfide, di(butylbenzyl)sulfide, di(pentylbenzyl)sulfide, di(hexylbenzyl)sulfide, di(octylbenzyl)sulfide, di(methylphenyl)sulfide and dibenzyl sulfide; compounds in which a hydrocarbon compound and an aromatic hydrocarbon compound are bonded via an ether bond, such as methoxybenzene, ethoxybenzene, butoxybenzene, dimethoxybenzene, diethoxybenzene, and dibutoxybenzene; halides such as chloromethane, chloroethane, chloropentane, chlorooctane, bromomethane, bromoethane, bromopentane, bromooctane, dichloroethane, dichloropentane, dichlorooctane, dibromoethane, dibromopentane, dibromooctane, chlorobenzene, bromobenzene, dichlorobenzene, dibromobenzene, benzyl chloride and benzyl bromide; alcohols such as methanol, ethanol, propanol, butanol and hexanol; monosubstituted phenols such as phenol, ethylphenol, propylphenol, butylphenol, pentylphenol, hexylphenol, heptylphenol, octylphenol and nonylphenol; and disubstituted phenols such as dimethylphenol, diethylphenol and dipropylphenol.

Among them, compounds having an ether bond or a thioether bond, such as (B), (D) or (E), sometimes produce oxides or peroxides depending on conditions. Among them, from the viewpoint of being thermally stable, (A) hydrocarbon compounds having a straight-chain, branched-chain or cyclic structure, (C) aromatic hydrocarbon compounds which may have a substituent composed of a hydrocarbon group, and (F) halides in which at least one hydrogen atom constituting a hydrocarbon compound having a straight-chain, branched-chain or cyclic structure, or at least one hydrogen atom constituting an aromatic hydrocarbon compound which may have a substituent comprising a hydrocarbon group is replaced by a halogen atom are preferable. Moreover, compounds containing a halogen atom, such as (F), sometimes decompose or generate halogen radicals such that halides are mixed in a product depending on conditions, and thus, (A) hydrocarbon compounds having a straight-chain, branched-chain or cyclic structure, (C) aromatic hydrocarbon compounds which may have a substituent composed of a hydrocarbon group, and (G) hydroxy compounds are further preferable.

The amount of the low-boiling compound used is not particularly limited, but if a too large amount of the low-boiling compound is used, the volume of the gas phase sometimes becomes too large as compared to the volume of the liquid phase in the flow channel 2, thereby resulting in the cause of a reduction in the amount of production, and thus, it is preferably 0.5 wt % to 50 wt %, and more preferably 1 wt % to 40 wt % with respect to the mixture containing the raw material compound.

<Flow Channel>

The flow channel 2 for performing the reaction step, which is used in the present embodiments, may be anything, and it may be a flow channel composed of a tube made of metal or resin, or a flow channel composed of a plurality of flat plates. Moreover, it may be composed of a single flow channel or may be formed by combining a plurality of flow channels.

The flow channel 2 preferably has a specific surface area of 10 $m^2/m^3$ or more and less than 1000 $m^2/m^3$. When the specific surface area of the flow channel 2 exceeds 1000 $m^2/m^3$, the gas-liquid interfacial area is reduced by unification of the gas and the liquid in the flow channel, and effects by the present embodiments sometimes cannot be sufficiently exerted. From this viewpoint, the specific surface area of the flow channel 2 is more preferably less than 700 $m^2/m^3$, and further preferably less than 500 $m^2/m^3$. On the other hand, when the specific surface area of the flow channel 2 is less than 10 $m^2/m^3$, the distribution resistance in the flow channel becomes too large, and the treatment efficiency is sometimes reduced. From this viewpoint, the specific surface area of the flow channel 2 is more preferably 20 $m^2/m^3$ or more, and further preferably 50 $m^2/m^3$ or more.

As the equivalent diameter, the lower limit of the inner diameter of the flow channel 2 is preferably 5 µm or more, more preferably 10 µm or more, further preferably 50 µm or more, and most preferably 100 µm or more. Moreover, the upper limit of the inner diameter of the flow channel 2 is preferably 50 mm or less, more preferably 5000 µm or less, and most preferably 2500 µm or less. When the equivalent diameter of the microtubule reactor exceeds 50 mm, the gas-liquid interfacial area is reduced by unification of the gas and the liquid in the flow channel, and effects by the present embodiments sometimes cannot be sufficiently exerted. On the other hand, when it is less than 5 µm, the distribution resistance in the flow channel becomes too large, and the treatment efficiency is sometimes reduced.

The term "equivalent diameter" in the present embodiments is defined as a diameter of a circle having the same area as the cross section perpendicular to the flow direction of the flow channel. When the cross section is a perfect circle, its diameter is the equivalent diameter. The shape of the cross section of the flow channel in the present embodiments is not particularly limited, and those having various shapes such as circular, elliptical, square, rectangular, and other polygonal shapes can be used.

The length of the flow channel 2 is determined such that the reacting fluid is retained in the reactor for a sufficiently long time so as to progress a reaction. When the length of the reactor is increased for the purpose of lengthening retention time, in order to avoid equipment from getting larger, the reactor may be a coil shape.

For the purpose of supplying the amount of heat required for the reaction from the wall surface of the flew channel with high efficiency, the material constituting the flow channel 2 is preferably a material having high thermal conductivity. Moreover, since the intensity with respect to the inner pressure of the flow channel needs to be secured depending on reaction conditions, a material which excels in mechanical strength is preferable. Specific examples include metals, glass, quartz and organic polymers. Although the metals may be simple substances or alloys, iron, copper, nickel, stainless and hastelloy can be used, and among them, a stainless-steel tube is suitably used. The thickness of the reactor made of these materials is not particularly limited.

In the present embodiments, as the state of the gas-liquid multiphase flow flowing in the flow channel 2, plug flow in which a gas plug and a liquid plug flow alternately, slug flow in which a gas plug and a liquid slug flow alternately, bubble flow, chum flow, annular flow, annular dispersed flow, plug flow, stratified flow and wavy flow can be applied, and in particular, plug flow or slug flow having a large gas plug that almost fills the cross section of the flow channel has a large retention time increasing effect due to a reduction in the volume of gas, and is preferable as the state of the gas-liquid multiphase flow.

The state of the gas-liquid multiphase flow in the reactor can be confirmed by connecting a flow channel having a transmission part and visually contacting or photographing it, or by a direct method such as visualization of the inside by high-speed X-ray CT, a method by measurement of the physical state of the gas-liquid multiphase flow, such as confirmation by classification based on the statistical nature of a differential pressure fluctuating signal of the flow channel, a method by computation simulation, and the like.

<Reaction Conditions>

The reaction pressure when performing the reaction step may be any of reduced pressure, ordinary pressure and increased pressure, and can be selected according to a reaction to be performed and properties of a low-boiling component to be used. Regarding the reaction temperature, a conventionally-used condition can be used, and it is selected from a range in which the lower limit is preferably 80° C. or more, more preferably 100° C. or more, and further preferably 130° C. or more, and the upper limit is preferably 1000° C. or less, more preferably 500° C. or less, further preferably 300° C. or less, and most preferably 250° C. or less.

Regarding the supply of the raw material compound and the low-boiling compound to the flow channel 2 in which the reaction step is performed, the mixture containing the raw material compound, and the low-boiling compound may be separately supplied, or a single mixture containing the raw material compound and the low-boiling compound is prepared to be supplied as described above.

The mixture to be supplied to the flow channel 2 may contain a reaction solvent. The reaction solvent is contained in the liquid phase in the reaction step. The reaction solvent being a liquid indicates the case where the boiling point of the raw material is higher than the reaction temperature.

As the reaction solvent, for example, alkanes such as pentane, hexane, heptane, octane, nonane and decane; aromatic hydrocarbons and alkyl-substituted aromatic hydrocarbons such as benzene, toluene, xylene, ethylbenzene, diisopropylbenzene, dibutylbenzene and naphthalene; nitrile compounds such as acetonitrile and benzonitrile; aromatic compounds substituted by halogen or a nitro group, such s chlorobenzene, dichlorobenzene, bromobenzene, dibromobenzene, chloronaphthalene, bromonaphthalene, nitrobenzene and nitronaphthalene; polycyclic hydrocarbon compounds such as diphenyl, substituted diphenyl, diphenylmethane, terphenyl, anthracene and dibenzyltoluene; aliphatic hydrocarbons such as cyclohexane, cyclopentane, cyclooctane and ethylcyclohexane; ketones such as methyl ethyl ketone, and acetophenone; esters such as dibutyl phthalate, dihexyl phthalate, dioctyl phthalate and benzyl butyl phthalate; ethers and thioethers such as tetrahydrofuran, 1,4-dioxane, 1,2-dimethoxyethane, diphenylether and diphenyl sulfide; ketone compounds such as acetone and methyl ethyl ketone; ester compounds such as ethyl acetate and ethyl benzoate; and sulfoxides such as dimethylsulfoxide and diphenylsulfoxide are suitably used. Obviously, one or a plurality of raw materials is excessively used in the reaction, and the excess can also be used as the reaction solvent.

In addition, depending on the reaction, a catalyst can be added to the mixture containing the raw material compound and the low-boiling compound as necessary.

The supply rate of the liquid containing the raw material compound and the low-boiling compound is not particularly limited, and can be determined in consideration of the volume of the flow channel 2, the retention time, and time required for heating.

In the reaction step, the reaction product and the gas component are manufactured by a heating reaction. In the present step, the low-boiling compound is preferably evaporated. More specifically, in the reaction step, the low-boiling compound is evaporated, the reaction product and the gas component are produced from the raw material compound by the heating reaction, and the gas phase containing the gas component and the evaporated low-boiling compound is formed in the flow channel 2.

It is preferable that the temperature of the reaction step exceed the boiling point of the low-boiling solvent and be less than the boiling point of the raw material compound. It is to be noted that, in the case of containing two or more low-boiling compounds or raw material compounds, the temperature of the reaction step is set with respect to the boiling point of the compound having the highest boiling point.

[Separation Step]

The reaction liquid which has been passed through the flow channel 2 is supplied to a gas-liquid separator 104. In the gas-liquid separator 104, the reaction liquid is separated into the liquid phase containing the reaction product and the gas phase containing the gas component and the low-boiling compound. It is to be noted that the liquid phase sometimes contains an unreacted raw material compound. The separation of the liquid phase from the gas phase is preferably performed by gas-liquid separation. A method and equipment of the gas-liquid separation are not particularly limited, and a known method can be used, and for example, the gas-liquid separation may be performed by connecting the flow channel 2 to a flash tank, a distillation column or the like. The gas phase component is passed through a flow channel 4 together with nitrogen gas supplied from a flow channel 3 as necessary, cooled in a condenser 107, and collected in a tank 105. On the other hand, the liquid phase component is passed through a flow channel 5 forming a U-tube, and collected in a tank 106. Preferably, the separation of the liquid phase containing the reaction product from the gas phase containing the gas component and the low-boiling compound is performed in the gas-liquid separator 104, and the flow channel 2 at a connection between the gas-liquid separator 104 and the flow channel 2 is in a state of being inclined at 5° or more to the horizontal surface. Being inclined at 5° or more may be upward or downward, and is preferably downward.

More specifically, preferably, the equipment for performing the method according to the present embodiments includes the gas-liquid separator 104 for performing the separation of the liquid phase containing the reaction product from the gas phase containing the gas component and the low-boiling compound, and the flow channel 2 at the connection between the gas-liquid separator 104 and the flow channel 2 is inclined at 5° or more to the horizontal surface. By using such equipment, a gas-liquid separation property is improved. The mechanism for exerting such an effect is not clear, but the present inventors presume that it is because a tendency to facilitate separation of droplets of the liquid phase component, which are susceptible to the influence of gravity, from the gas phase which is insusceptible to the influence of gravity is strengthened when the anti-liquid phase and the gas phase are supplied to the gas-liquid separator 104 from the flow channel 2. From such a viewpoint, the inclination to the horizontal surface is preferably 10° or more, and more preferably 20° or more.

<Reaction Product>

The reaction product in the present embodiments is manufactured from the raw material compound made of one or a plurality of compounds by the heating reaction accompanied by production of the gas component.

<Gas Component>

The gas component is a component that becomes gas under conditions where the reaction step is performed, and can be variously selected depending on conditions where the reaction is performed. Whether it is a component that becomes gas under the conditions where the reaction step is performed can be determined, for example, by reference to the vapor pressure of the compound in the reaction conditions.

The gas component produced by the reaction in the manufacturing method of the present embodiments is preferably at least one selected from the group consisting of water, ammonia, amine compounds, hydroxy compounds, thiol compounds and hydrogen.

Examples of the amine compounds include monoalkylamines such as methylamine, ethylamine, propylamine, butylamine, and hexylamine, dialkylamines such as dimethylamine, diethylamine, dipropylamine, dibutylamine and dihexylamine, aromatic monoamines such as aniline, methylaniline and dimethylaniline, and aromatic diamines such as diphenylamine. It is to be noted that, in the case where a plurality of isomers exist in the compounds which are specifically exemplified in the present specification, they include these isomers.

Examples of the hydroxy compounds include alcohols such as methanol, ethanol, propanol, butanol, hexanol and octanol, and aromatic hydroxy compounds such as phenol.

Examples of the thiol compounds include thiol compounds such as methanethiol, ethanethiol, propanethiol, butanethiol, hexanethiol and phenylthiol.

Hereinafter, reaction examples for producing the reaction product and the gas component in the present embodiments will be illustrated.

<Reaction that Produces Water>

Examples of a reaction in which the gas component produced by the reaction is water include at least one reaction selected from the group consisting of functional group reactions represented by formulas (1) and (2).

[Chemical Formula 5]

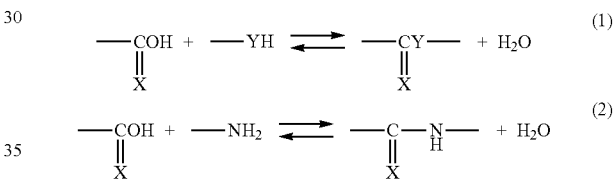

In the formulas, X and Y each independently represents an oxygen atom or a sulfur atom.

The reactions are expressed by focusing attention on the functional groups in formulas (1) and (2), but these compounds having functional groups may be monofunctional or multifunctional.

For example, when the compounds in formulas (1) and (2) are all monofunctional, formulas (1) and (2) can be expressed as formulas (1)' and (2)', respectively.

[Chemical Formula 6]

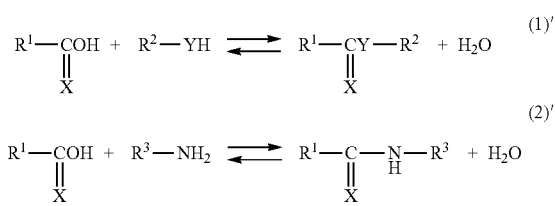

In the formulas, $R^1$, $R^2$, and $R^3$ each independently represents an aliphatic group or an aromatic group, and X and Y each independently represents an oxygen atom or a sulfur atom.

Moreover, for example, when the compounds in formulas (1) and (2) are all bifunctional, formulas (1) and (2) can be expressed as formulas (1)" and (2)", respectively.

[Chemical Formula 7]

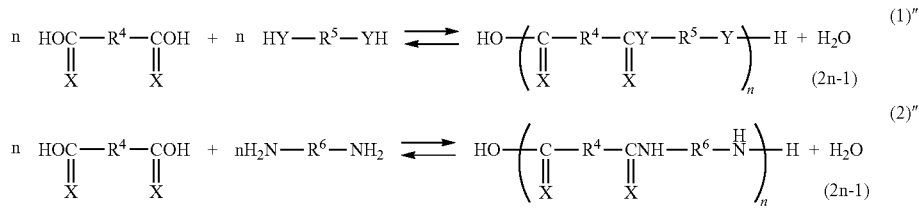

In the formulas, $R^4$, $R^5$ and $R^6$ each independently represents a bifunctional aliphatic group or a bifunctional aromatic group, and X and Y each independently represents an oxygen atom or a sulfur atom.

It is to be noted that, in the reactions including the functional group reactions represented by formulas (1) and (2), the compounds to be reacted (compounds of left member in each formula) need not to be monofunctional or multifunctional at the same time as expressed by formulas (1)' and (2)', and formulas (1)" and (2)", and may be a combination of a monofunctional compound and a multifunctional compound.

In the above formulas, examples of $R^1$ to $R^6$ preferably include an aliphatic group having 1 to 20 carbon atoms or an aromatic group having 6 to 20 carbon atoms.

In the above formulas, examples of $R^1$ to $R^6$ preferably include a group derived from straight-chain hydrocarbons such as methane, ethane, propane, butane, pentane, hexane and octane; a group derived from alicyclic hydrocarbons such as cyclopentane, cyclohexane, cycloheptane, cyclooctane and bis(cyclohexyl)alkanes; a group derived from substituted cyclohexanes such as methylcyclopentane, ethylcyclopentane, methylcyclohexane, ethylcyclohexane, propylcyclohexane, butylcyclohexane, pentylcyclohexane and hexylcyclohexane; a group derived from dialkyl-substituted cyclohexanes such as dimethylcyclohexane, diethylcyclohexane and dibutylcyclohexane; a group derived from trialkyl-substituted cyclohexanes such as 1,5,5-trimethylcyclohexane, 1,5,5-triethylcyclohexane, 1,5,5-tripropylcyclohexane and 1,5,5-tributylcyclohexane; a group derived from monoalkyl-substituted benzenes such as toluene, ethylbenzene and propylbenzene; a group derived from dialkyl-substituted benzenes such as xylene, diethylbenzene and dipropylbenzene; and a group derived from aromatic hydrocarbons such as diphenylalkanes and benzene.

<Reaction that Produces Ammonia>

Examples of a reaction in which the gas component produced by the reaction is ammonia include at least one reaction selected from the group consisting of functional group reactions represented by formulas (3) to (8). In the formulas, X, Y and Z represent the groups defined as above.

[Chemical Formula 8]

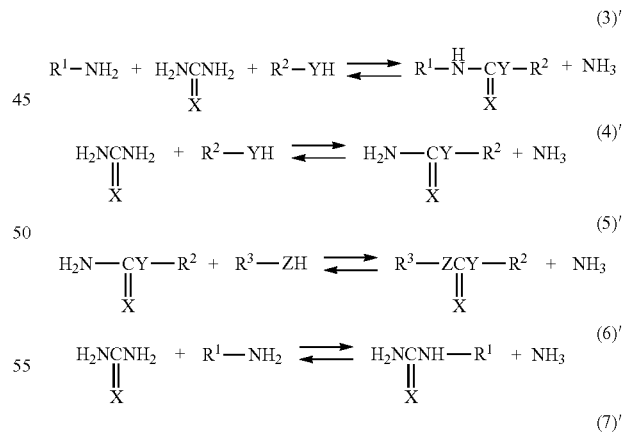

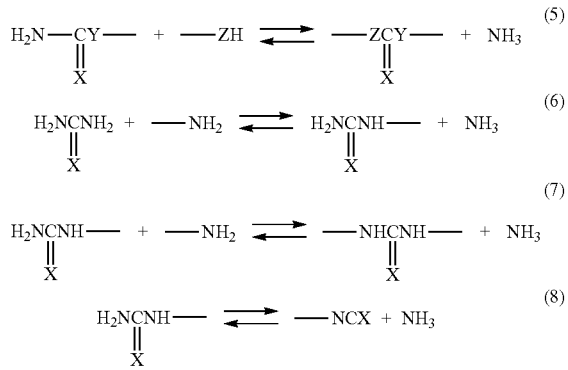

The reactions are expressed by focusing attention on the functional groups in formulas (3) to (8), but these compounds having functional groups may be monofunctional or multifunctional.

For example, when the compounds in formulas (3) to (8) are all monofunctional, formulas (3) to (8) can be expressed as formulas (3)' to (8)', respectively. In the formulas, $R^1$, $R^2$, $R^3$, X, Y and Z represent the groups defined as above.

[Chemical Formula 9]

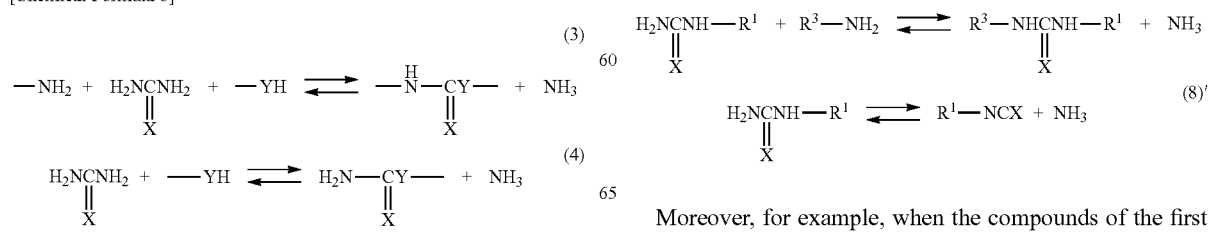

Moreover, for example, when the compounds of the first term of the left member in formula (3), the second term of the left member in formula (6), the first term and the second term of the left member in formula (7), and the left member in formula (8) are all bifunctional, formulas (3), (6) and (8) can be expressed as formulas (3)″, (6)″ and (8)″, respectively. In the formulas, $R^2$, $R^4$, X and Y represent the groups defined as above.

[Chemical Formula 10]

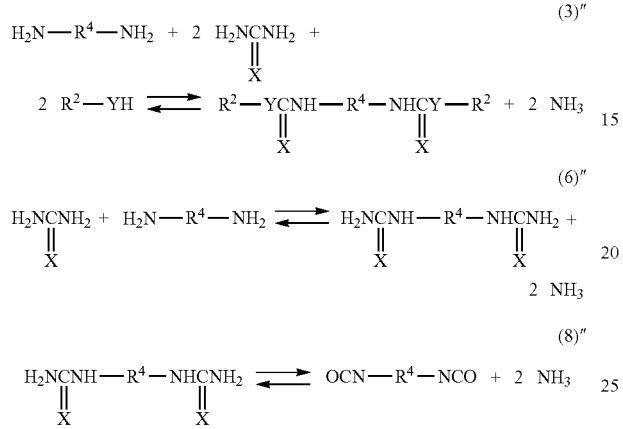

It is to be noted that the reactions including the functional group reactions represented by formulas (3) to (8) can be applied without the need to be a combination of a monofunctional compound and a multifunctional compound as expressed by formulas (3)′ to (8)′, (3)″, (6)″ and (8)″.

<Reaction that Produces Amine>

Examples of a reaction in which the gas component produced by the reaction is an amine include reactions including at least one reaction selected from the group consisting of functional group reactions represented by formulas (9) to (11). In the formulas, X, Y and Z represent the groups defined as above.

[Chemical Formula 11]

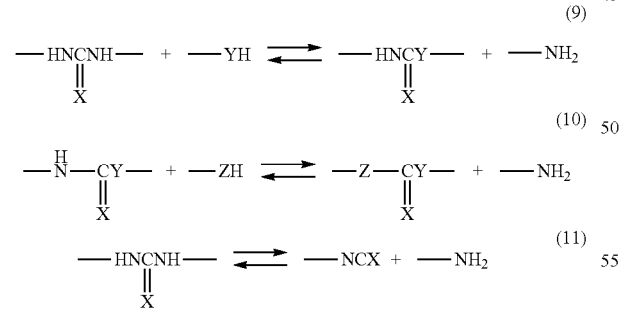

The reactions are expressed by focusing attention on the functional groups in formulas (9) to (11), but these compounds having functional groups may be monofunctional or multifunctional.

For example, when the compounds in formulas (9) to (11) are all monofunctional, formulas (9) to (11) can be expressed as formulas (9)′ to (11)′, respectively. In the formulas, $R^1$, $R^2$, $R^3$, X, Y and Z represent the groups defined as above.

[Chemical Formula 12]

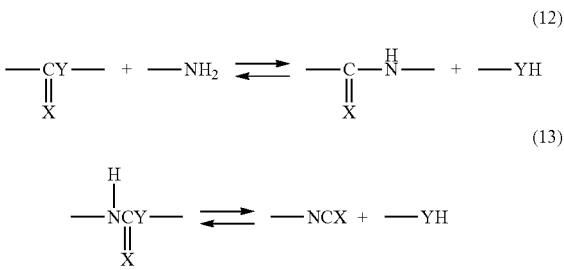

It is to be noted that the reactions including the functional group reactions represented by formulas (9) to (11) may be a reaction of a multifunctional compound or a reaction of a multifunctional compound and a monofunctional compound.

<Reaction that Produces Hydroxy Compound or Thiol Compound>

Examples of a reaction in which the gas component produced by the reaction is a hydroxy compound or a thiol compound include reactions including at least one reaction selected from the group consisting of functional group reactions represented by formulas (12) and (13). In the formulas, X and Y represent the groups defined as above.

[Chemical Formula 13]

$$\text{—CY—} + \text{—NH}_2 \rightleftarrows \text{—C—N—} + \text{—YH} \quad (12)$$
$$\text{—NCY—} \rightleftarrows \text{—NCX} + \text{—YH} \quad (13)$$

The reactions are expressed by focusing attention on the functional groups in formulas (12) and (13), but these compounds having functional groups may be monofunctional or multifunctional.

For example, when the compounds in formulas (12) and (13) are all monofunctional, formulas (12) and (13) can be expressed as formulas (12)′ and (13)′, respectively. In the formulas, $R^1$, $R^2$, $R^3$, X and Y represent the groups defined as above.

[Chemical Formula 14]

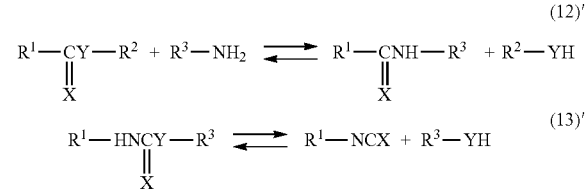

Moreover, for example, when the left member and the first term of the right member are bifunctional compounds and the second term of the right member is a monofunctional compound in formula (13), formula (13) can be expressed as formula (13)". In the formula, $R^3$, $R^4$, X and Y represent the groups defined as above.

[Chemical Formula 15]

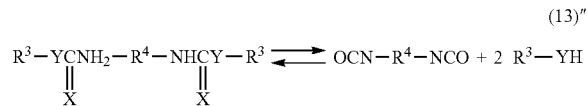

(13)″

It is to be noted that the reactions including the functional group reactions represented by formulas (12) and (13) may be a reaction of a multifunctional compound or a reaction of a multifunctional compound and a monofunctional compound.

Moreover, the reaction in which the gas component produced by the reaction is a hydroxy compound or a thiol compound is an ester exchange reaction of a hydroxy compound or a thiol compound with an ester compound, and may be an ester exchange reaction in which the ester compound is at least one ester compound selected from the group consisting of carboxylate esters, thiocarboxylate esters, carbonate esters, carbamate esters and thiocarbamate esters.

Specific examples of the reaction include reactions represented by formulas (14) to (16). It is to be noted that reactions of monofunctional compounds are expressed in formulas (14) to (16), but multifunctional compounds can be applied in the same manner. In the formulas, $R^1$, $R^2$, $R^3$, X, Y and Z represent the groups defined as above.

[Chemical Formula 16]

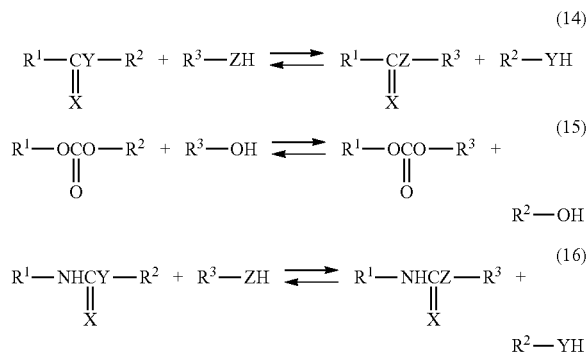

According to the present invention, since a gas phase is made to exist in a flow channel, a single liquid containing a raw material compound and a low-boiling compound is used as a liquid to be introduced into the flow channel, and therefore, a reaction method in which processing of equipment for separately supplying a gas phase and a liquid phase, and the control of a gas phase and a liquid phase in the flow channel are easy can be provided. Furthermore, according to the present invention, a reaction method capable of easily increasing the number of flow channels for industrial practice can be provided.

EXAMPLES

The present invention will be described in further detail with reference to Examples and Comparative Examples, but the technical range of the present invention and embodiments thereof are not limited to these.

Example 1

Equipment shown in FIG. 1 was used. Both the flow channel 1 and the flow channel 2 are SUS316 tubes having an outer diameter of 1/16 inches and an inner diameter of 0.5 mm. The flow channel 2 is heated by the electric heater 103, and the length of the flow channel 2 which is being heated is 50 m.

100 g of phenol (1.09 mol), 43 g of urea (0.72 mol) and 10 g of toluene were mixed and put in the tank 101. The mixture in the tank 101 was supplied at 10 g per minute by the pump 102. The heating temperature of the flow channel 2 was set to 160° C. A reaction liquid which had been passed through the flow channel 2 was supplied to the gas-liquid separator 104 which had been heated at 100° C. The gas phase component containing ammonia and toluene in the gas-liquid separator 104 was passed through the flow channel 4 together with nitrogen gas supplied from the flow channel 3, cooled in the condenser 107, and transferred into the tank 105. On the other hand, the liquid phase component was passed through the flow channel 5 forming a U-tube, and transferred into the tank 106. When the mixture which was transferred into the tank 106 was analyzed with liquid chromatography, the mixture contained phenyl carbamate, and the yield with respect to urea was 42%.

Comparative Example 1

The same method as Example 1 was performed except that 100 g of phenol (1.09 mol) and 43 g of urea (0.72 mol) were mixed and toluene was not used. The mixture which was transferred into the tank 106 contained phenyl carbamate, and the yield with respect to urea was 6%.

Example 2

The same method as Example 1 was performed except that 100 g of acetic acid (1.67 mol), 300 g of isoamyl alcohol (3.40 mol) and 20 g of tetrahydrofuran were used and the heating temperature of the flow channel 2 was set to 105° C. The gas phase component containing tetrahydrofuran and water was passed through the flow channel 4, cooled in the condenser 107, and transferred into the tank 105. The mixture which was transferred into the tank 106 contained isoamyl acetate, and the yield with respect to acetic acid was 81%.

Comparative Example 2

The same method as Example 2 was performed except that 100 g of acetic acid (1.67 mol) and 300 g of isoamyl alcohol (3.40 mol) were used and tetrahydrofuran was not used. The yield of isoamyl acetate with respect to acetic acid was 34%.

Example 3

The same method as Example 1 was performed except that 116 g of hexamethylenediamine (1.00 mol), 150 g of urea (2.50 mol), 1840 g of phenol (20.0 mol) and 110 g of toluene were used and the heating of the flow channel 2 was set to 180° C. The gas phase component containing toluene and ammonia was passed through the flow channel 4, cooled in the condenser 107, and transferred into the tank 105. The mixture which was transferred into the tank 106 contained N,N'-hexanediyl-di(phenyl carbamate), and the yield with respect to hexamethylenediamine was 32%.

Comparative Example 3

The same method as Example 3 was performed except that 116 g of hexamethylenediamine (1.00 mol), 150 g of urea (2.50 mol) and 1840 g of phenol (20.0 mol) were used and toluene was not used. The yield of N,N'-hexanediyl-diphenyl carbamate) with respect to hexamethylenediamine was 4%.

Example 4

The same method as Example 1 was performed except that 202 g of 1,6-hexanediurea (1.00 mol), 2470 g of 4-tert-octylphenol (12.0 mol) and 180 g of toluene were used and the heating of the flow channel 2 was set to 220° C. The gas phase component containing toluene and ammonia was passed through the flow channel 4, cooled in the condenser 107, and transferred into the tank 105. The mixture which was transferred into the tank 106 contained N,N'-hexanediyl-di((4-tert-octylphenyl)carbamate), and the yield with respect to hexamethylenediamine was 44%.

Comparative Example 4

The same method as Example 4 was performed except that 202 g of 1,6-hexanediurea (1.00 mol) and 2470 g of 4-tert-octylphenol (12.0 mol) were used and 180 g of toluene was not used. The yield of N,N'-hexanediyl-di((4-tert-octylphenyl)carbamate) with respect to hexamethylenediamine was 5%.

Example 5

The same method as Example 1 was performed except that 50 g of 2,4-toluenediurea, 820 g of dibenzyl ether and 20 g of tetrahydrofuran were used and the heating of the flow channel 2 was set to 200° C. The gas phase component containing tetrahydrofuran and ammonia was passed through the flow channel 4, cooled in the condenser 107, and transferred into the tank 105. The mixture which was transferred into the tank 106 contained 2,4-toluene diisocyanate, and the yield with respect to 2,4-toluenediurea was 89%.

Comparative Example 5

The same method as Example 5 was performed except that 50 g of 2,4-toluenediurea and 820 g of dibenzyl ether were used and tetrahydrofuran was not used. The yield of 2,4-toluene diisocyanate with respect to 2,4-toluenediurea was 15%.

REFERENCE SIGNS LIST

1, 2, 3, 4, 5: flow channel, 102: pump, 103: heater, 104: gas-liquid separator, 105, 106: tank, 107: condenser.

The invention claimed is:
1. A reaction method accompanied by production of a gas component, comprising the steps of:
supplying a liquid containing at least one raw material compound and a low-boiling compound having a standard boiling point lower than a standard boiling point of the raw material compound to a flow channel;
heating the liquid to produce a liquid reaction product and a gas component by a reaction of the raw material compound; and
separating a liquid phase containing the reaction product from a gas phase containing the gas component and the low-boiling compound in a gas-liquid separator located outside of the flow channel, wherein the flow channel supplies the gas component only to the gas-liquid separator,
wherein the flow channel has a specific surface area of 10 $m^2/m^3$ or more and less than 1000 $m^2/m^3$, and an equivalent diameter of the flow channel is 50 mm or less, wherein the flow channel has only one outlet, wherein the gas component contains at least one selected from the group consisting of water, ammonia, an amine compound, a hydroxy compound and a thiol compound.
2. The method according to claim 1, wherein a stoichiometric proportion of the raw material compound to the reaction product in the liquid is raw material compound: reaction product=100:0 to 80:20.
3. The method according to claim 1, wherein the low-boiling compound is collected as a component contained in the gas phase and/or the liquid phase.
4. The method according to claim 1, wherein the gas phase containing the gas component and the low-boiling compound is produced in the flow channel.
5. The method according to claim 1, wherein the standard boiling point of the low-boiling compound is lower than the standard boiling point of the raw material compound by 10° C. or more.
6. The method according to claim 1, wherein the gas component contains water, and the reaction includes at least one reaction selected from the group consisting of functional group reactions represented by formulas (1) and (2):

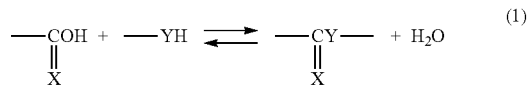

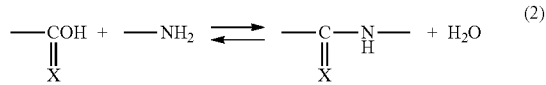

wherein X and Y each independently represents an oxygen atom or a sulfur atom.
7. The method according to claim 1, wherein the gas component contains ammonia, and the reaction includes at least one reaction selected from the group consisting of functional group reactions represented by formulas (3) to (8):

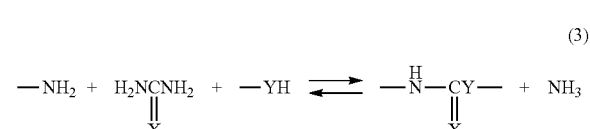

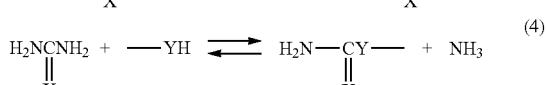

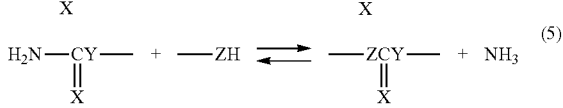

-continued

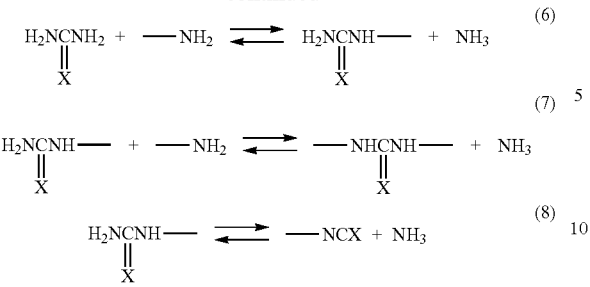

wherein X, Y and Z each independently represents an oxygen atom or a sulfur atom.

8. The method according to claim 1, wherein the gas component contains an amine compound, and the reaction includes at least one reaction selected from the group consisting of functional group reactions represented by formulas (9) to (11):

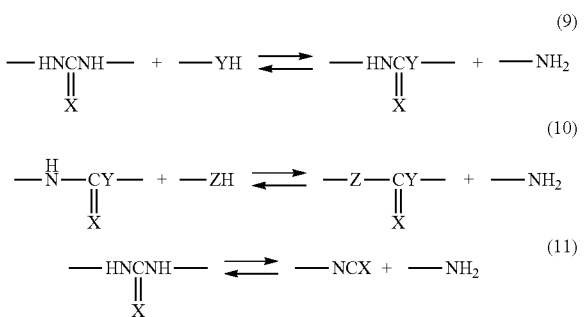

wherein X, Y and Z each independently represents an oxygen atom or a sulfur atom.

9. The method according to claim 1, wherein the gas component contains a hydroxy compound or a thiol compound, and the reaction includes at least one functional group reaction selected from the group consisting of functional group reactions represented by formulas (12) and (13):

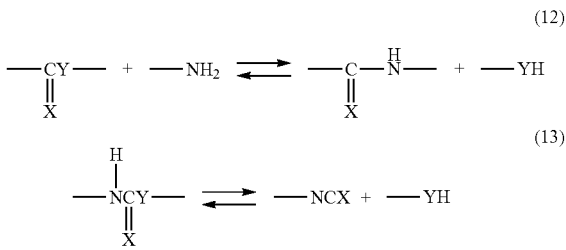

wherein X and Y each independently represents an oxygen atom or a sulfur atom.

10. The method according to claim 1, wherein the gas component contains a hydroxy compound or a thiol compound, the reaction is an ester exchange reaction that is a reaction of a hydroxy compound or a thiol compound with an ester compound, and the ester compound is at least one ester selected from the group consisting of a carboxylate ester, a thiocarboxylate ester, a carbonate ester, a carbamate ester and a thiocarbamate ester.

11. The method according to claim 1, wherein the flow channel is heated to 80° C. or more, and the low-boiling compound is a compound having a standard boiling point of 50° C. or more.

12. The method according to claim 2, wherein the low-boiling compound is collected as a component contained in the gas phase and/or the liquid phase.

13. The method according to claim 2, wherein the gas phase containing the gas component and the low-boiling compound is produced in the flow channel.

14. The method according to claim 2, wherein the standard boiling point of the low-boiling compound is lower than the standard boiling point of the raw material compound by 10° C. or more.

15. The method according to claim 1, wherein the flow channel at a connection between the gas-liquid separator and the flow channel is inclined at 5° or more to a horizontal surface.

* * * * *